United States Patent [19]
Rhea, Jr.

[11] Patent Number: 5,916,153
[45] Date of Patent: Jun. 29, 1999

[54] MULTIFUNCTION CATHETER

[76] Inventor: W. Gardner Rhea, Jr., 101 Boring Cir., Lafayette, La. 70506

[21] Appl. No.: 08/958,509

[22] Filed: Oct. 27, 1997

[51] Int. Cl.⁶ ....................................................... A61B 5/00
[52] U.S. Cl. .............................. 600/310; 600/339; 604/96
[58] Field of Search ........................... 600/310, 322–325, 600/339–342, 364, 549, 585, 473, 474, 476, 478, 479; 604/96

[56] References Cited

U.S. PATENT DOCUMENTS

| | | | |
|---|---|---|---|
| 5,246,016 | 9/1993 | Lieber et al. | 600/341 |
| 5,389,217 | 2/1995 | Singer | 604/96 |
| 5,415,165 | 5/1995 | Fiddian-Green | 600/364 |

Primary Examiner—Cary O'Connor
Assistant Examiner—Eric F. Winakur
Attorney, Agent, or Firm—John D. Jeter

[57] ABSTRACT

A modified Foley type catheter has a pressure sensor near the insertion end, an inflatable balloon, a temperature sensor, a light emitter, and a blood oxygen level detector near the light emitting means, all molded into the catheter tube wall. The oxygen level sensor is arranged to receive light energy from tissue illuminated by the light source. All required electrical conductors, and fiber optics elements if used, are molded into the catheter wall and terminate in a connector near the access end. The balloon has a fluid supply conduit, or channel, molded into the catheter wall and it terminates in a connector nipple near the access end. A pulse detector means is derived from the association of the oxygen level sensor and the required external signal processor. All associated external signal processor and output indicators means currently exist for observation and recording. Rewiring for suitable connector association with the novel catheter is well established in the art.

8 Claims, 1 Drawing Sheet

MULTIFUNCTION CATHETER

This invention pertains to a medical catheter for insertion into the human body. More particularly, the catheter is adapted for, but not limited to, insertion along the urethra into the bladder to measure various vital signs as well as to drain the bladder.

BACKGROUND OF THE INVENTION

In trauma and many operative cases it is customary to insert a catheter into the bladder very early on to drain the bladder, detect some forms of internal damage, and monitor urinary output, and potentially provides passage for insertion of other instruments. Temperature measurements can be readily made by way of the catheter duct with electronic sensors now available. Internal pressure, intra-abdominal, may need to be monitored in many cases and here also electronic related sensors provide means to monitor pressure by way of the catheter access. The mucosa lining the genito-urinary and gastrointestinal tracts has vascular features that facilitate blood oxygen level determinations. The usual practice involves the use of a light source and a light sensitive sensor, attached to available body areas, that indicates oxygen level in the blood by it's light response characteristics. Externally applied, these systems sometimes become dislodged. Modern light sources and sensors suggest the use of the catheter structure as convenient access for oximeter functions. The vessels of the mucosa pulse with the heartbeat and provide a convenient pulse rate detector with readily available adaptation of the electronic signal processor activity related to the blood oxygen sensor.

The development of miniature sensors and closely related signal carriers invited and was attended by an increase in the number of data gathering functions considered necessary. The apparatus grew smaller but the number increased. The work area became cluttered. Connections of monitoring devices to external instrumentation became more tedious and invited errors. The loss of monitor information at critical points was, and is, dangerous.

There is a need to combine a number of medical data gathering intrusive devices into the envelope of one of those devices deemed necessary so that the effect of only one intrusion is borne by the patient and patient care area. Further, when time is assumed to be vital, the use of a single catheter, capable of a plurality of functions, is of value in terms of time economy and certainty of correct connections. In addition, the security of device placement and the acquisition of reliable data, being critical, is significantly advanced by the combination of these modalities.

It is therefore an object of this invention to provide via the catheter apparatus a combination of data gathering functions in one catheter envelope.

It is yet another object of this invention to provide a urethral catheter with a built in temperature measuring capability, a built in pressure measuring capability, a built in blood oxygen measuring capability and a built in pulse rate measuring ability, with a balloon near the insertion end of the catheter for anchoring the assembly within the urinary bladder, thus assuring the correct and stable placement of the various monitoring devices.

These and other objects, advantages, and features of this invention will be apparent to those skilled in the art from a consideration of this specification, including the attached claims and appended drawings.

SUMMARY OF THE INVENTION

A modified Foley catheter has fluid conduits molded into the tube wall material to provide a passage to inflate a balloon near the insertion end for anchoring the catheter in the body. Wire conductors, and fiber optics elements if used, imbedded in the catheter structure provide power and sensor related circuits for a light near the insertion end, a temperature sensor, a pressure sensor and a blood oxygen level sensor. The associated external instrumentation, not part of this disclosure, provides power control and interpreter functions for the light, the pressure sensor, and the temperature sensor. The oxygen sensor reacts to the light characteristics as modified by vascular content between the light source and the sensor and, in conjunction with associated external signal processing means, alluded to above, processes the signal to provide an indication of the level of oxygen in the blood. The instrumentation related to the oxygen sensing action can, within the realm of current art, responds to the pulsation of light received by that sensor and provide signal conditioning ability to indicate pulse rate. No additional conductors and sensors are needed for the pulse sensing function. The light source and oximeter sensor emit and receive through a thin portion of the catheter wall. The catheter, in general, follows the well known Foley configuration.

BRIEF DESCRIPTION OF DRAWINGS

In the drawings wherein like features have similar captions.

DETAILED DESCRIPTION OF DRAWINGS

Figure 1:
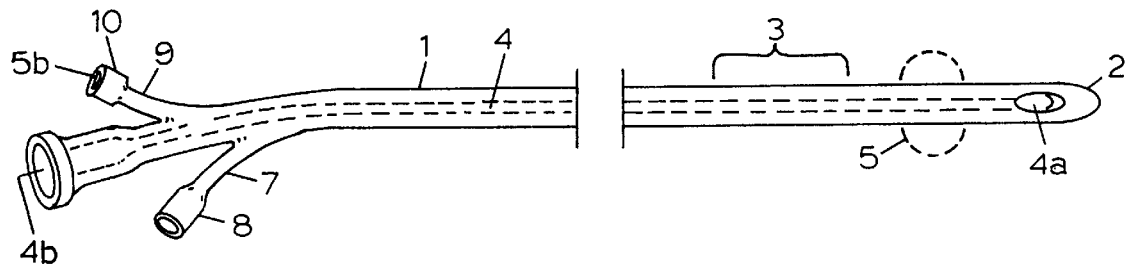
FIG. 1 is a side view of the novel catheter.

In the drawings certain features well established in the art and not bearing upon points of novelty are omitted in the interest of descriptive clarity. Such omitted features may include layered structure of the general embodiment.

In FIG. 1, tubular body 1 is terminated by funnel opening end 4b at the access end and tapered insertion end 2. The usual generally central catheter conduit 4 extends from the common opening 4b at the access end to the dual openings 4a near the tip of the insertion end. The retention balloon 5 is shown inflated by dashed lines. Intrinsic light sources and sensors distributed along length 3, yet to be described, depend upon the usual external control and signal processing means to be connected by the multi-conductor connector 8 pending from neck 7. Preferably, all imbedded conductors terminate in one connector. External circuitry demands may dictate separate connectors for different groups of conductors in which case more than one connector, pending from related necks, will be used. The balloon requires a fluid conduit, described later, and that conduit terminates in opening 5b in nipple 10 pending from neck 9.

Figure 2:
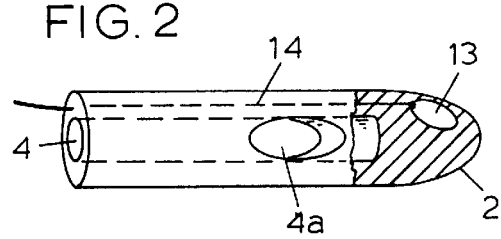
FIG. 2 is a fragmentary side view, somewhat enlarged, and partially cut away, of the insertion end of the novel catheter.

In FIG. 2, the insertion end is enlarged and passage end 4 is shown to open from the sides 4a of the point 2. Element 13 is a pressure sensor of a miniature type that is commonly available and is imbedded, or molded, into the wall of the end portion of the catheter. Wires 14, probably two, are imbedded in the catheter general structure.

Figure 3:
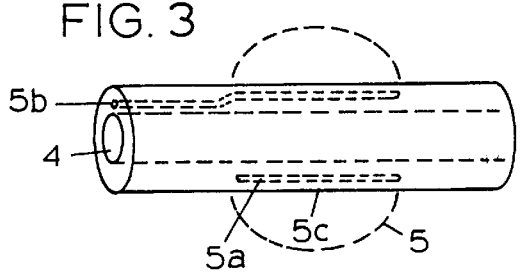
FIG. 3 is a side view, similar in scale of that of FIG. 2 but showing an area farther yet from the insertion end.

FIG. 3 relates to a balloon arrangement that is used to anchor the catheter within the body. Annular plenum, or peripheral chamber, 5a, with a thin membrane outer shroud 5c, is intrinsic to the catheter tube, sometimes attached as a membrane sleeve, surrounds the catheter body and is fluidly connected with channel 5b by which the annular space can be expanded by inflation to provide a bulge 5 on the catheter to anchor it in the body. This balloon structure is common to the well known Foley catheter. Dashed lines illustrate the expansion nature of the balloon feature.

Figure 4:
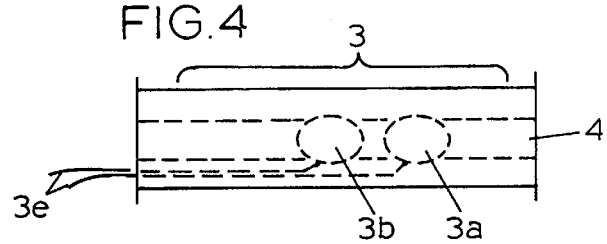
FIG. 4 is a side view, similar in scale to that of FIG. 2 but showing a region farther from the insertion end in the region captioned as 3 in FIG. 1.

FIG. 4 shows the light emitting device, fiber optic or diode, 3a molded into the catheter wall and arranged to emit light outward through a covering compatible with the catheter purpose. The light sensitive sensor 3b, also molded into the catheter wall, is arranged to receive light, fluorescently responsive to or reflected from the surrounding tissue in response to light projected from source 3a. The sensor is selected and arranged to produce an electrical output characteristic that is related to the blood oxygen concentration in the illuminated tissue. The sensor is dependent upon external signal processor means to be accessed by conductors imbedded, or molded into, the catheter wall and those conductors are captioned as a group 3e emerging from the cutaway catheter. Conductors shown are symbolic and may involve several individual conductors as required by the particular contrivances specified. When associated with external signal processor means, the sensor, as a pulse and oximeter component, is old art and currently available.

Figure 5:
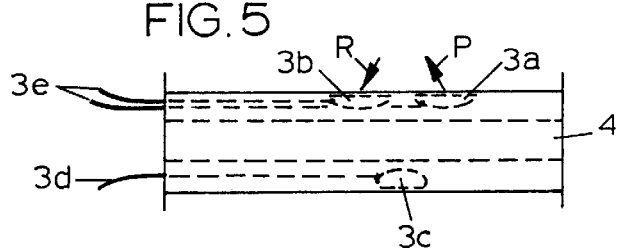
FIG. 5 is an orthogonal view of the view of FIG. 4.

FIG. 5 is an orthogonal projection of FIG. 4. Temperature sensor 3c, not visible in FIG. 4, is imbedded in the catheter wall and has an associated conductor means 3d, also embedded. Arrows P and R represent light paths permitted by the catheter outer material. The conductor means may include a ground line common to all electrical contrivances in the catheter, all of which will eventually lead to the connector 8. The temperature sensor is old art, when associated with external signal processor means.

Well established in the instrumentation art the light source and sensors defined herein and accessible by way of connector 8 will be supplied with a specification known as "pin outs" that relate the characteristics of the imbedded electrical contrivances. From the "pin out" specifications, instrument specialists define the related external signal conditioner and indicator, including recorder, systems that empower the catheter user to utilize the catheter system for the intended purpose. Every sensor intrinsic to the novel catheter is now in use in the medical community in one form or another and the total functions defined herein can be achieved by a plurality of available devices. In the realm of patient management related activities, the plurality is a problem in that an assembly of individual systems take time, space, attention to detail, and generally clutter up a busy environment where time saved, certainty of function, and simplicity of installation can save lives.

It will be understood that certain features and sub-combinations are of utility and may be employed without reference to other features and sub-combinations. This is contemplated by and is within the scope of the claims.

As many possible embodiments may be made of the catheter of this invention without departing from the scope thereof, it is to be understood that all matter herein set forth or shown in the accompanying drawings is to be interpreted as illustrative and not in a limiting sense.

The invention having been described, I claim:

1. A catheter device arranged to empower a plurality of functions with a single insertion operation, the catheter comprising:

a) a urethral-type catheter having an insertion end and an access end and a connecting tube;

b) a pressure sensor imbedded into said insertion end;

c) a temperature sensor imbedded into the wall of said tube, near said insertion end and arranged to produce an electric signal with characteristics determined by temperature sensed;

d) a light emitter imbedded into said wall and arranged to project light outward from the outside surface of said tube in response to electric energy provided thereto;

e) a color discriminating light sensitive detector molded into the wall of said tube and arranged to produce an electric signal with characteristics determined by the characteristics of light energy received from the urethral lining outside said catheter;

f) an inflatable balloon intrinsic to said catheter tube wall, near said insertion end, comprising a peripheral chamber in said tube wall;

g) a plurality of conductors imbedded in said catheter wall, at least one connected to each said light emitter, said light sensitive detector, said temperature sensor, and said pressure sensor, each terminating in an at least one conductor connector near said access end; and h) a fluid conductor tube imbedded in said catheter wall, fluidly connected to said peripheral chamber and opening as a tubular connector extending from said catheter near said access end;

whereby said light detector, when in use adjacent mucosa, receives light energy produced by said light source as conditioned by said mucosa and whereby said catheter provides a terminal end for association with external signal conditioner, control, and indicator means.

2. The catheter of claim 1 wherein said at least one conductor is connected to said catheter by a flexible extension.

3. The catheter of claim 1 wherein said pressure sensor is imbedded near the outer surface of said wall.

4. The catheter of claim 1 wherein said balloon is situated along said catheter tube between said insertion end and said temperature sensor.

5. The catheter of claim 1 wherein said balloon is situated along said catheter tube between said insertion end and said light emitter and light sensitive detector.

6. The catheter of claim 1 wherein said light emitter and said light detector are covered by a thin membrane that provides the outer surface of said catheter.

7. The catheter of claim 1 wherein said peripheral chamber is, at least in part, provided by a tubular membrane secured to the external surface of said catheter.

8. A modified Foley catheter having an insertion end, an access end, and a tubular extension therebetween comprising intrinsic pressure sensor means, temperature sensor means, and oximeter means imbedded in the material forming the wall of the tubular extension and provided with at least one electrical connector at the access end, said connector providing access to conductors imbedded in the wall and in communication with said connector and external control and signal conditioning means to provide readout information defining temperature, pressure, blood oxygen levels and pulse rate for a patient fitted with the catheter.

* * * * *